(12) United States Patent
Schudel et al.

(10) Patent No.: US 7,166,567 B2
(45) Date of Patent: Jan. 23, 2007

(54) FRAGRANCE COMPOSITIONS (75) Inventors: Markus Schudel, Zürich (CH); Christian Quellet, Biel (CH); Marc Taschi, Zofingen (CH); Johnny Bouwmeesters, Oetwil am See (CH)

(73) Assignee: Givaudan SA, Vernier (CH)

( * ) Notice: Subject to any disclaimer, the term of this patent is extended or adjusted under 35 U.S.C. 154(b) by 289 days.

(21) Appl. No.: 10/432,452

(22) PCT Filed: Nov. 15, 2001

(86) PCT No.: PCT/CH01/00671

§ 371 (c)(1),
(2), (4) Date: May 20, 2003

(87) PCT Pub. No.: WO02/41709

PCT Pub. Date: May 30, 2002

(65) Prior Publication Data

US 2004/0029750 A1 Feb. 12, 2004

(30) Foreign Application Priority Data

Nov. 21, 2000 (EP) ................................. 00124384

(51) Int. Cl.
C11D 17/08 (2006.01)
(52) U.S. Cl. ....................................................... 510/441
(58) Field of Classification Search ................ 510/101, 510/349, 438; 512/4
See application file for complete search history.

(56) References Cited

U.S. PATENT DOCUMENTS

| | | | |
|---|---|---|---|
| 3,922,354 A | 11/1975 | Galluzzi et al. ............. 426/96 |
| 4,842,761 A | 6/1989 | Rutherford ................... 252/90 |
| 5,126,061 A * | 6/1992 | Michael ....................... 510/106 |
| 6,056,949 A | 5/2000 | Menzi et al. ............... 424/76.1 |
| 6,403,186 B1 * | 6/2002 | Tararuj et al. ............. 428/40.1 |

FOREIGN PATENT DOCUMENTS

| | | |
|---|---|---|
| CN | 1047335 A | 11/1990 |
| EP | 0 070 719 | 1/1983 |
| EP | 0 397 246 A2 | 11/1990 |
| FR | 2 774 389 | 8/1999 |
| WO | 97 16078 | 5/1997 |

OTHER PUBLICATIONS

PCT International Search Report, dated Feb. 11, 2002, for PCT/CH01/00671.
Abstract of FR 2774389 from EPO website.

* cited by examiner

Primary Examiner—John R. Hardee
(74) Attorney, Agent, or Firm—Norris McLaughlin & Marcus PA (57) ABSTRACT

A composition comprising a fragrance material consisting of an outer matrix containing components of the fragrance material and disposed within the outer matrix, discrete core particles containing the remaining components of the fragrance material. Components of the fragrance material within the core particles are preferably selected from highly volatile and/or water soluble materials, whereas components of the fragrance material within the outer matrix are preferably selected from relatively low volatile and/or low water soluble materials.

22 Claims, 1 Drawing Sheet

FIGURE 1:

FRAGRANCE COMPOSITIONS

The present invention relates to compositions for delivering fragrance materials in a controlled manner, consumer product formulations containing said compositions and methods of forming same.

Prior art techniques for perfuming consumer products such as laundry products have consisted of mixing fragrance material directly to the consumer product. The disadvantage of such an approach is that some of the fragrance material is lost to the atmosphere during storage or through chemical degradation. Furthermore, in a wash cycle, fragrance materials are released rapidly and uncontrollably to the wash liquor whereupon large amounts may be lost to evaporation and dissolution rather than depositing onto a fabric.

The prior art has attempted to address this problem, and there are many disclosures of compositions intended for controlling release of fragrances into wash liquors. Such compositions typically comprise fragrance material in a matrix which matrix modulates the release of said fragrance material. In U.S. Pat. No. 4,842,761 a controlled release composition is described which contains a plurality of fragrance-containing phases each of which releases the fragrance sequentially during washing cycle, rinsing cycle and the drying process. However, a problem with this approach is that during each part of the cycle, the composition releases all of the components of a fragrance material into the washing, rinsing or drying media. This approach does not take into account that fragrance materials are complex mixtures of components having disparate physicochemical properties such as volatility, solubility and chemical reactivity. As such, the components tend to evaporate, dissolve and degrade at different rates and to different extents during storage and during each phase of a laundry cycle. Releasing all fragrance components together during a laundry cycle results in the disproportionate loss of highly volatile or soluble components (so-called <<Top Notes>>) through evaporation or dissolution, leaving the less volatile components or less soluble components (so-called <<Middle Notes>> or <<End Notes>>) to deposit onto a fabric. As the special character of a fragrance material (the so-called <<hedonic character>>) relies on the contribution of all components of a fragrance material, the character of a fragrance added to such compositions may change markedly as a result of prolonged storage or during a laundry cycle, such that the character of the fragrance material finally deposited onto a fabric no longer resembles the original character of the fragrance material.

Clearly, the hedonic character is a unique differentiator of a fragrance material that can offer a significant marketing advantage. Accordingly, there is a need for a composition that can selectively control the release of certain components of a fragrance material to ensure that the character of a fragrance material added to a consumer product, e.g. a laundry product, is reliably transferred to an article to be treated.

Furthermore, given that fragrances are considered by many end users to be commodity products, fragrance-containing compositions should be made of relatively cheap materials, be produced according to an economical process, and be capable of achieving a high loading of fragrance material and good retention of the fragrance during manufacture, storage and handling.

Applicant has developed a composition that solves the problems described above. Accordingly, the invention provides in a first aspect a composition for delivering a fragrance material comprising an outer matrix containing a fraction of the components of the fragrance material and disposed within the outer matrix, discrete core particles containing the remaining components of the fragrance material.

The composition according to the present invention provides the formulator far greater latitude in the control of the hedonic character of the fragrance material he chooses to employ. For example, relatively highly volatile, water-soluble or chemically unstable fragrance components may be disposed within the core particles which affords protection from external influences such as moisture and oxidative influences, and a controlled or retarded release of these components. Less volatile or less water-soluble components of a fragrance material may be contained in the outer matrix, as these components are more robust and are less prone to loss through evaporation or dissolution within an aqueous media. Having regard to the particular fragrance material employed and the physicochemical properties of components thereof, the skilled person could, without applying any inventive thought, determine which components should be included in the outer matrix material and which should be included in the particle matrix in order to achieve a desired hedonic effect.

Fragrance materials for use in the present invention may be selected from natural products such as essential oils, absolutes, resinoids, resins, concretes, and synthetic perfume components such as hydrocarbons, alcohols, aldehydes, ketones, ethers, acids, acetals, ketals and nitrites, including saturated and unsaturated compounds, aliphatic, carbocyclic and heterocyclic compounds. Other examples of odorant compositions which may be used are described in H 1468 (United States Statutory Invention Registration).

Preferred components of a fragrance material for addition to the outer matrix are substances that have a Loss Factor ($F_L$) that is lower than $10^2$ Pa ppm. The term <<Loss Factor>> refers to a parameter that is related to the losses of fragrance material during drying and is defined as the product of the pure component vapour pressure (Pa) and the water solubility (ppm) at room temperature. Vapour pressures and water solubility data for commercially available fragrance components are well known and so the Loss Factor for a given fragrance component may be easily calculated. Alternatively, vapour pressure and water solubility measurements may be easily taken using techniques well known in the art. Vapour pressure of fragrance components may be measured using any of the known quantitative headspace analysis techniques, see for example Mueller and Lamparsky in Perfumes: Art, Science and Technology, Chapter 6 "The Measurement of Odors" at pages 176–179 (Elsevier 1991). The water solubility of fragrances may be measured according to techniques known in the art for the measurement of sparingly water-soluble materials. A preferred technique involves the formation of a saturated solution of a fragrance component in water. A tube with a dialysed membrane is placed in the solution such that after equilibration an idealised solution is formed within the tube. The tube may be removed and the water solution therein extracted with a suitable organic solvent to remove the fragrance component. Finally the extracted fragrance component may be concentrated and measured, for example using gas chromatography. Other methods of measuring fragrances are disclosed in Gygax et al, Chimia 55 (2001) 401–405.

Examples of preferred fragrance components are any of those fragrances selected from Aldron, Ambrettolide, Ambroxan, Benzyl Cinnamate, Benzyl Salicylate, Boisambrene Forte, Cedrol Crystals, Cedryl Acetate Crystals, Celestolide/Crysolide, Cetalox, Citronellyl Ethoxalate, Fixal, Fixolide, Galaxolide 50 DEP, Guaiacwood Acetate, Cis-3-Hexenyl Salicylate, Hexyl Cinnamic Aldehyde, Hexyl Salicylate, Iso E Super, Linalyl Benzoate FCC, Linalyl Cinnamate, Linalyl Phenyl Acetate, Methyl Cedryl Ketone, Musk CPD, Musk Ketone, Musk Tibetine, Musk Xylol, Myraldyl Acetate, Nerolidyl Acetate, Novalide, Okoumal, Para Cresyl Caprylate, Para Cresyl Phenyl Acetate Crystals, Phantolid Crystals, Phenyl Ethyl Cinnamate, Phenyl Ethyl Salicylate, Rosone, Sandela (Lin), Tetradecanitrile, Thibetolide, Traseolide 100, Trimofix O.

Preferred components of a fragrance material for inclusion in the core particles are substances with a Loss Factor ($F_L$) higher than $10^2$ Pa ppm, most preferably higher than $10^4$ Pa ppm. Preferred fragrances may be selected from 2-Methyl Pyrazine, Acetaldehyde phenylethyl propyl acetal, Acetophenone, Alcohol C6 (in the following the notation Cn comprises all substances having n carbon atoms and one hydroxyl function), Alcohol C8, Aldehyde C6 (in the following the notation Cn encompasses all isomers having n carbon atoms and one aldehyde function), Aldehyde C7, Aldehyde C8, Aldehyde C9, Nonenylic Aldehyde, Allyl Amyl Glycolate, Allyl Caproate, Amyl Butyrate, Aldehyde Anisique, Benzaldehyde, Benzyl Acetate, Benzyl Acetone, Benzyl Alcohol, Benzyl Butyrate, Benzyl Formate, Benzyl Iso Valerate, Benzyl Methyl Ether, Benzyl Propionate, Bergamyl Acetate, Butyl Acetate, Camphor, 3-Methyl-5-propyl-2-cyclohexenone, Cinnamic Aldehyde, Cis-3-Hexenol, Cis-3-Hexenyl Acetate, Cis-3-Hexenyl Formate, Cis-3-Hexenyl Iso Butyrate, Cis-3-Hexenyl Propionate, Cis-3-Hexenyl Tiglate, Citronellal, Citronellol, Citronellyl Nitrile, 2Hydroxy-3-methyl-2-Cyclopenten-1 Cuminic Aldehyde, Cyclal C, Acetic Acid (cycloheyloxy)-2-propenylester, Damascenone, Damascone Alpha, Damascone Beta, Diethyl Malonate, Dihydro Jasmone, Dihydro Linalool, Dihydro Myrcenol, Dihydro Terpineol, Dimethyl Anthranilate, Dimethyl Benzyl Carbinol, Dimethyl Benzyl Carbinyl Acetate, Dimethyl Octenone, Dimetol, Dimyrcetol, Estragole, Ethyl Acetate, Ethyl Aceto Acetate, Ethyl Benzoate, Ethyl Heptoate, Ethyl Linalool, Ethyl Salicylate, Ethyl-2-Methyl Butyrate, Eucalyptol, Eugenol, Fenchyl Acetate, Fenchyl Alcohol, 4-Phenyl-2,4,6-trimethyl 1,3-dioxane, Methyl 2-octynoate, 4-Isopropylcyclohexanol, 2-sec-Butylcyclohexanone, Styralyl acetate, Geranyl nitrile, Hexyl Acetate, Ionone Alpha, iso Amyl Acetate, Iso Butyl Acetate, Iso Cyclo Citral, Dihydroisojasmone, Iso Menthone, Iso Pentyrate, Iso Pulegol, cis-Jasmone, Laevo Carvone, Phenylacetaldehyde glycerylacetal, carbinic acid 3-Hexenyl Methyl Ether, 1-Methyl-cyclohexa-1,3-diene, Linalool, Linalool Oxide, 2,6-Dimethyl-5-heptenal, Menthol, Menthone, Methyl Acetophenone, Methyl Amyl Ketone, Methyl Benzoate, Methyl Cinnamic Aldehyde Alpha, Methyl Heptenone, Methyl Hexyl Ketone, Methyl Para Cresol, Methyl Phenyl Acetate, Methyl Salicylate, Neral, Nerol, 4-tert-Pentyl-cyclohexanone, Para Cresol, Para Cresyl Acetate, Para Tertiary Butyl Cyclohexanone, Para Tolyl Aldehyde, Phenyl Acetaldehyde, Phenyl Ethyl Acetate, Phenyl ethyl alcohol, Phenyl ethyl butyrate, Phenyl ethyl formate, Phenyl ethyl iso butyrate, Phenyl ethyl propionate, Phenyl Propyl Acetate, Phenyl Propyl Aldehyde, Tetrahydro-2,4-dimethyl-4-pentyl-furan, 4-Methyl-2-(2-methyl-1-propenyl)tetrahydropyran, 5-Methyl-3-heptanone oxime, Styralyl Propionate, Styrene Monomer, 4-Methylphenylacetaldehyde, Terpineol, Terpinolene, Tetrahydro Linalool, Tetrahydro Myrcenol, Trans-2-Hexenal, 4,7-Methano-1H-3A,4,5,6,7, 7A-hexahydro-acetate and Viridine.

The skilled person will appreciate that the outer matrix and the core particles constitute discrete phases that may serve to separate fragrance components according to selection criteria based on their physicochemical properties. As described above, the separation of fragrance components is made on the basis of the Loss Factor of the fragrance components, however, one could additionally separate fragrance components that would otherwise be reactive if they were mixed together and stored for any length of time. Accordingly, the present invention may provided interesting fragrance accords that would otherwise not be possible if all fragrance components were mixed together. Still further, the skilled person would appreciate that different core particles may contain different fragrance components. Such an embodiment would potentially provide opportunities for additional controlled release of selected components to give yet further interesting fragrance effects.

In a preferred embodiment of the present invention the outer matrix consists of a matrix substance ($S_2$) and the core particles consist of a matrix substance ($S_1$), wherein $S_1$ and $S_2$ may be the same or different and are hydrophilic materials that may be selected from:

(1) Carbohydrates such as (i) monosaccharides; (ii) oligosaccharides; (iii) polysaccharides; (iv) starches including modified starches and hydrolysates; (v) hydrogenates of (i–iv). Both linear and branched carbohydrate chains can be used. In addition, chemically modified starches and poly-/oligo-saccharides may be used including the addition of hydrophobic moieties of the form of alkyl, or aryl;(vi) sucrose esters, glycerol esters like tripalminate, tristearate, palmito stearate, or behenate;

(2) Natural or synthetic gums such as alginate esters, carrageenan, xanthanes, agar-agar, pectines, pectic acid, and natural gums such as gum arabic, gum tragacanth and gum karaya;

(3) Chitin and cationic polysaccharides like chitosan derivatives, salts and mixtures thereof;

(4) Cellulose and cellulose derivatives such as (i) cellulose acetate and cellulose acetate phthalate; (ii) hydroxy methyl propyl cellulose; (iii) carboxy methyl cellulose; hydroxy propyl methyl cellulose phthalate, hydroxy propyl methyl cellulose acetate succinate and their salts; (iv) all enteric/aquateric coatings and mixture thereof;

(5) Polypeptides such as (i) plant proteins, e.g. hydrolyzed oat proteins; (ii) animal proteins, e.g. gelatin, collagen, elastin, or keratin, and their hydrolyzed or quaternized derivatives; (iii) proteins of synthetic origin, e.g. homopolymers and copolymers produced by polycondensation of amino acids like aspartamic and glutamic acid, glycine, alanine, or leucine;

(6) Synthetic water soluble or partially water soluble, or degradable polymers such as (i) vinyl polymers like poly(vinyl alcohol), poly(vinyl alcohol-co-vinyl acetate) copolymers, poly(vinyl alcohol-co-vinyl acetate-co-sodium vinyl sulfonate) copolymers; poly(vinyl pyrrolidon) and copolymer derivatives such as poly(vinyl pyrrolidon-co-vinyl acetate), poly(vinylpyrrolidon-co-vinylalcohol), poly(vinylpyrrolidon-co-styrene); (ii) alkali-soluble polymers, e.g. poly(acrylic acid), poly(maleic acid), poly (alkyl(meth)acrylate-co-(meth)acrylic acid) copolymer, poly(acrylic acid-co-maleic acid)copolymer, poly(acrylamide), poly(methacrylic acid), poly((meth)acryl amide) as well as other acrylic homo- and copolymers thereof; (iii) polyoxides, polyethers and poly(ethyleneimine), e.g. poly(ethyleneoxide), poly-(propyleneoxide), poly(vinylmethylether), poly-(ethyleneimine), and their mixture and salts; (iv) poly(vinyloxazolidone) and poly(vinyl methyl oxazolidone), partially esterified copolymers of methyl vinyl ether and maleic anhydride like poly(vinylether-co-maleic anhydride) and its acid forms; (v) silicone polyglucoside derivatives such as poly (dimethicone-co-ethoxy glucoside) copolymer derivatives or mixtures thereof;

(7) Polyelectrolytes such as poly (ethylene imine) derivatives or poly (acrylic acid) derivatives or mixture thereof;

(8) Biodegradable (bio)polymers such as (i) polyesters, especially lactic, glycolic, hydroxybutyric acid derivatives such as poly (D,L-lactide), poly (L-lactide), poly (L-lactide-co-glycolide), poly(D,L-lactide-co-glycolide), poly (D,L-lactide-co-glycolide-D-glucose), poly (hydroxybutyric acid) and further derivatives, copolymers or mixtures thereof; (ii) water soluble or water dispersible forms of poly (3-hydroxy butyrate) derivatives; (iii) lignin derivatives such as lignosulphonates, oxylignins and kraft lignins and further derivatives or mixture thereof;

(9) Plasticizers such as triacetin, triethylcitrate, polyethylene glycol, diethyl phthalate, tributyl citrate, glycerin or other conventional plasticizers and their mixtures; and (10) Inorganic materials such as silicates, phosphates, borates, acetates, sulphates, oxides, hydroxides, clay minerals, zeolites in colloidal or standard form.

The core particle matrix substance $S_1$ and outer matrix substance $S_2$ may independently be solids, and essentially non-porous and water- or alkali-soluble or swellable. More preferably, they are glassy and non-sticky and have a glass transition temperature $T_g$ that is higher than room temperature. Such matrix materials provide fragrance materials with good protection from moisture and oxidative influences and act to substantially prevent leaching of fragrance materials from the particles during manufacture and storage. They may also act as a means of controlling the release of fragrance components.

Disposed within the matrix substances $S_1$ and $S_2$ may be emulsifiers $E_1$ and $E_2$ respectively. Emulsifiers $E_1$ and $E_2$ may be the same or different and may be selected from a mixture of octenyl succinate-substituted starch and a non substituted starch, e.g. Capsul® or Hi-Cap 100®; sucrose esters such as Sisterna PS750® or synthetic polymers such as poly (vinyl alcohol), e.g. Mowiol®, or derivatives in combination with suitable surface active agents. Instead of using only a mixture of octenyl succinate-substituted starch and a non-substituted starch, long chain glycosides such as sucrose esters, optionally combined with short chain emulsifiers, such as sorbates, sorbitan esters and their ethoxylated derivatives may be employed. Furthermore, a blend of modified starch-free emulsifiers and modified starch octenyl succinate emulsifiers can be used.

Preferably, fragrance material components may be disposed within the core particles and in the outer matrix in the form of finely dispersed droplets. Hereinafter such droplets in the core particles are referred to as <<Inclusions $I_1$>>, whereas those disposed within the outer matrix are referred to as <<Inclusions $I_2$>>. Preferably, these Inclusions have diameters of 0.1 to 20 microns, particularly 0.1 to 5 microns, more particularly 0.1 to 1 micron.

In addition to containing components of fragrance materials, the Inclusions may comprise carrier materials. Carrier materials provided in $I_1$ and $I_2$ are referred to as $C_1$ and $C_2$ respectively. The carrier material $C_1$ and carrier material $C_2$ may be the same or different and may be selected from hydrophobic liquid diluents, waxes, resins, surfactants, and polymers belonging to one or more of the following categories:

(1) Silicones and modified silicones, e.g. linear, ramified or crosslinked poly (dialkylsiloxane) and modified poly(dialkylsiloxane) containing polyether, e.g. those materials disclosed in WO 01/25389, alkyl, and glycoside side chains, as well as silicones bearing quaternized ammonium functions;

(2) Polymers obtained by radical polymerization of monomers containing an activated carbon-carbon double bond like vinyl, styrenyl and acryl monomers; or polymers obtained by polycondensation or polyaddition.

(3) polyolefins; and (4) Alkali-soluble polymers., and (5) Surfactants selected from anionic, cationic, zwitterionic and non-ionic surfactants, e.g. alkyl sulphates, quaternized trialkylammonium salts, alkylglycosides, alkylethoxylates, alkylphenylethoxylates, or amphiphilic block and graft copolymers such as polyoxyethylene-polyoxypropylene-polyoxyethylene triblock-copolymers, polyethylene-polyoxyethylene diblock copolymers, or silicones grafted with alkyl chains and polyether chains.

$C_1$ and $C_2$ may be independently solvents or diluents which are water insoluble, e.g. hydrophobic liquids such as isopropyl myristate, miglyol, mineral oil or dibenzyl ether. Preferably, however, they are in the form of a wax, a resin or a polymer obtained by polymerization of monomers containing an activated carbon-carbon double bond such as vinyl and acrylic monomers. Preferred carriers may be used to minimize the evaporation tendency of very volatile fragrance material components.

Carrier materials may also be employed as support materials for the fragrance material components, which may be deposited in or on said carrier materials. The carrier materials may help retain the fragrance materials in their respective Inclusions during storage and handling, and may affect the way in which fragrance material partitions between wash-liquor/air and wash-liquor/fabric interfaces during a wash cycle, thereby to promote improved deposition on fabrics.

Inclusions $I_1$ may be present in the core particles in amounts of up to 80% based on the total weight of particles. Inclusions $I_2$ may be present in the outer matrix in amounts of up to 75% based on the total weight of the outer matrix.

Inclusions $I_1$ may contain 30 to 100%, more preferably 50 to 100% by weight of fragrance material components. Inclusions $I_1$ may contain up to 50% by weight of carrier material $C_1$. Similarly, Inclusions $I_2$ may contain 30 to 100%, more preferably 50 to 100% by weight of fragrance material. Inclusions $I_2$ may contain up to 50% by weight of carrier $C_2$.

A function of emulsifiers $E_1$ and $E_2$ is to ensure that fragrance material and optionally carrier material can be dispersed in, or emulsified with, an aqueous phase during the manufacture of the compositions according to the invention. Emulsifiers are therefore provided in sufficient amounts to ensure that fragrance material, and optionally carrier material, are dispersed in a stable fashion in the aqueous phase or that a stable oil-in-water emulsion might be formed. The minimum amount of emulsifier need to form monolayer around the Inclusions can be calculated according to techniques well known in the art, and in particular by considering the interfacial area of the Inclusions and the area of the interface that would be occupied by one molecule of a given emulsifier. Thereafter, an amount of emulsifier in excess of the amount needed to form a monolayer may be employed to take into account that the emulsifier will partition between the interface and the aqueous phase, for example in accordance with its HLB value. In a preferred embodiment, the emulsifier will be employed in an at least 10 fold excess. For commercially available emulsifiers having HLB values of 12 to 18, it is preferred to employ the emulsifier in a mass ratio $I_1:E_1$ or $I_2:E_2$ of lower than 25:2. This ratio is particularly preferred in the case of modified starch emulsifiers, in particular combinations of octenyl succinate-substituted starch and a non substituted starch, e.g. Capsul® or Hi-Cap 100®. Reference to <<mass>> used in relation to the ratios $I_1:E_1$ and $I_2:E_2$, is a reference to the active mass of the emulsifier. For example, in the case of a combination of octenyl succinate-substituted starch and a non substituted starch, it is only the octenyl succinate-substituted starch that is active. The skilled person will appreciate that other emulsifier materials may be supplied in diluents and that the amounts of surfactant added to composition of the present invention should be adjusted accordingly.

Compositions according to the invention may additionally comprise a coating material. The coating material covers the composition and provides additional protection for the fragrance material. Preferably the material of the coating has hydrophobic, water repellent characteristics. It may be a fat, a fatty acid, a hydrophobized silicon dioxide, a silicone, a silicone-based wax, or a mixture thereof, a modified cellulose, a poly(vinyl alcohol-co-vinyl acetate) copolymer with a degree of hydrolysis preferably lower than 85% or higher than 91%, a partially lactonized poly(vinyl alcohol-co-acrylic acid) copolymer, a modified poly(vinyl alcohol) bearing aceto acetate groups, or a mixture thereof. The coating may also comprise a fragrance material. Adding fragrance components to the coating will allow the particulate material to emit a pleasant odour under dry storage conditions.

In a preferred embodiment the coating is a hydrogenated vegetable fat having a melting point ranging between 30 to 100° C. in order that it can perform in all possible wash cycles, preferably between 30 and 60° C., more preferably between 35 and 45° C. Other preferred coating materials are cellulose or cellulose derivatives, e.g. ethyl cellulose, as well as film forming synthetic polymers such as poly (vinyl alcohol), poly (vinyl acetate) or (vinyl butyral), or poly (vinyl pyrrolidone), or vinyl alcohol copolymers.

The composition may comprise other optional ingredients that may be conventionally employed in fragrance compositions, for example dyestuffs.

The compositions of the present invention may be provided in particulate form. Preferably, the particle size is between 0.1 and 2 mm. For powder application a size of particulate material between 0.1 and 1.5 mm is preferred, whereas for tablets a size of particulate material between 0.1 and 1 mm is preferred.

Compositions having the aforementioned particle size are advantageous for numerous reasons. Because the particles of this size are of comparable size to many powder formulations, e.g. powder detergents, the compositions according to the present invention may be easily mixed and formulated therewith. Furthermore, the relatively large particle sizes are more easily functionalised, e.g. they are more easily coated, than finer particle size material. Still further, the relatively large particle size provides for a mechanically stable and free flowing composition. However, large particles take time to build up, and during the manufacturing process fragrance components (particularly highly volatile and/or water-soluble components) may leach out of the particles during their formation, or otherwise degrade, for example due to high processing temperatures. Accordingly, it has generally been accepted that to obtain material having relatively large particle size, it is difficult to retain fragrance material However, applicant has found that by dividing fragrance material between core particles and the outer matrix it is possible to achieve large particle size material and yet have high loading, e.g. greater than 25%, more particularly greater than 30%, and retention after manufacture (so-called "Initial Retention") greater than about 80%, more particularly greater than 90%. Without wishing to be bound by any theory, applicant believes that this desirable result is achieved because a relatively high loading of fragrance material may be trapped and retained in the core particles (which are relatively small and therefore quickly formed) before the large diameter particulate material is built up by mixing the fragranced core particles with the outer matrix material.

Furthermore, applicant has found that controlling the mass ratio $I_1:E_1$ or $I_2:E_2$ promotes high loading of fragrance material and high initial retention. Still further, retention during storage (so-called <<aged retention>>) may also be very high, e.g. about 80% or more, more particularly about 90% or more. For example, a mass ratio $I_1:E_1$ or $I_2:E_2$ of lower than 25:2 (w/w) is particularly preferred when commercially available modified starch emulsifiers are used, e.g. combinations of octenyl succinate-substituted starch and a non substituted starch, e.g. Capsul® or Hi-Cap 100®.

Loss of fragrance components during manufacture is particularly a problem with the more volatile and/or water soluble components, e.g. those components having a Loss Factor higher than $10^2$ Pa ppm referred to hereinabove, and the skilled person will understand that the invention is particularly suitable for obtaining high loading and high retention of these types of components. However, the skilled person will also appreciate that the invention relates to a general approach of obtaining high fragrance loading and retention, such that portions of a complete fragrance material may be divided between core particles and outer matrix to achieve a desired result.

Compositions according to the invention may be formed with rather narrow particle size distribution, e.g. after protective screening (2 mm sieve) the distribution is such that 50%, more preferably 80% of the particles have diameters of 100 to 2000 microns, more particularly 200 to 1000 microns. Furthermore, the compositions preferably have a high bulk density, for example 0.3 to 1.5 g/cm$^3$, more preferably 0.5 to 0.9 g/cm$^3$. Accordingly, compositions are essentially dust-free, e.g. the composition may exhibit a fine particle fraction of less than 5% for particle sizes of less than 0.08 mm.

As has been described above, a considerable advantage of the present compositions is that the kinetics of release of individual or groups of fragrance material components can be controlled by dividing components between different parts of a composition. However, the judicious selection of the particular matrix substances $S_1$, $S_2$, the coating, and optionally the emulsifiers or carrier materials may exercise still further control of the kinetics. In particular, the duration and time dependence of the release can be controlled by controlling the thickness of the coating and/or by careful selection of particle matrix substance $S_1$, the emulsifier $E_1$, the outer matrix substance $S_2$, the emulsifier $E_2$ as well as the material of the coating. In the particular case of laundry detergents, it is preferred to employ a coating to ensure high protection of the granulate particle against moisture and chemical degradation in aggressive detergent bases. It has also been observed that selecting carefully the coating and matrix materials confers a high protection against humidity while keeping the disintegration process within a period of time commensurate with conventional machine wash cycles. In particular, by judiciously selecting the core particle matrix substance $S_1$, the emulsifier $E_1$, the outer matrix substance $S_2$ and the emulsifier $E_2$, as well as the coating, the release properties of the composition can be controlled in such a way that 80 to 90% of the fragrance material is delivered to the wash liquor within 15 to 30 minutes at 40° C., while the disintegration of the composition does not exceed 10 minutes.

Accordingly, the invention provides in another of its aspects a composition for the controlled release of a fragrance material during a wash cycle wherein the release profile is characterised by a latency period of at least 5 minutes during which time the concentration of fragrance material in a wash liquor reaches its maximum. Furthermore, as the concentration of a fragrance material in a headspace is directly related to the concentration in an aqueous wash liquor, it is possible to measure the maximum concentration in the liquor by simply performing a headspace analysis according to any of the techniques known in the art.

A composition having a release profile as hereinabove described has the advantage in that essentially all of the composition is disintegrated before the end of the wash cycle, wherein, by <<disintegrated>> is meant that material residues visible to the eye remain neither in suspension in the wash liquor or rinse liquor, nor on substrates treated with products containing said composition.

The invention is also directed to a method of forming a composition as hereinabove described comprising the steps of spraying the outer matrix material onto core particles to encapsulate said core particles. Optionally, the resultant encapsulated material can be coated with a coating material as hereinabove defined.

The outer matrix material may be sprayed onto particles in order to build-up compositions according to the invention. In order to build-up the composition, the outer matrix material must be sufficiently tacky to coat individual core particles and to permit individual core particles to stick together or agglomerate. The applicant has surprisingly found a relationship between the tack and the water content of the outer matrix material, and the size and size distribution of the particulate matter formed. Furthermore, tack and water content may also affect the loading and retention of fragrance material in said particulate material: Whereas the matrix material must contain a certain water content to provide requisite tack, too much water will promote leaching of fragrance material from the composition during manufacture and reduce both loading and retention. Furthermore, as the water has to evaporate, it will also increase manufacturing time which provides more time for leaching and/or degradation to occur.

Given that tack and water content are properties that are difficult to measure directly during manufacture, the tack of a particular outer matrix material during manufacture can be estimated based on equilibrium measurements on cast binder films. Thus, an emulsion of outer matrix material may be formed into a cast film by i) applying this emulsion to a glass surface with a calibrated application cylinder to produce a film of 100 microns thickness (+/–10%); ii) equilibrating the system in a climate chamber with a known constant relative humidity for at least 24 hours; iii) measuring the so-called <<Rolling Ball Tack>>, (described below) or estimating the finger tip grip of the film (according to the so-called <<Finger Tip Method>> described below); and iv) determining the equilibrium water content of the film by any of the water determination techniques that are well known in the art, such as thermogravimetry (TGA), IR spectroscopy or Karl Fischer titration.

Data obtained on cast binder films after equilibration at 70% relative humidity and 25° C. can be advantageously used to select appropriate outer matrix compositions to obtain compositions in particulate form having the desired particle size (and distribution), and fragrance material loading and retention. Those outer matrix materials that form 100 +/–10 micron cast films with an equilibrium water content at 70% relative humidity lower than 10% by weight, preferably lower than 5% by weight, and a <<rolling-ball tack>> value ranging between 4 cm and 20 cm, preferably between 6 cm and 15 cm, and most preferably between 8 and 12 cm, are preferred outer matrix materials for use in the present invention.

The Rolling Ball Tack measurement yields a convenient picture of the ability of the outer matrix material to adhere readily to a surface, i.e. to establish an adhesive bond with a surface within a time scale not exceeding 1 second. The rolling ball tack value is inversely related to the real tack. Hence, the lower the rolling-ball tack value (cm), the higher is the real tack and the faster the formation of an adhesive bond between the outer matrix material and a surface with which it comes into contact. For comparison, conventional adhesive tapes such as those commonly used in offices and households have a rolling ball tack value of 10 to 12 cm, while low temperature adhesives have a Rolling Ball Tack value not exceeding 2 to 5 cm. A description of the Rolling Ball Tack method can be found in *Tack Rolling Ball Test Method PSTC* 6, available from Pressure Sensitive Tape Council, page 19–64, 12. edition, August 1999.

An alternative to the Rolling Ball Tack Measurement is provided by the so-called <<finger tip method>>, that is, a method whereby one applies and removes a tip of one's finger onto an adhesive surface in order to estimate the grip of the adhesive. Outer matrix materials provided as cast films with a finger tip grip comparable to that of a conventional adhesive tape, after equilibration at 70% relative humidity and 25° C., are particularly suitable for the purpose of the present invention.

The outer matrix material may be applied to the core particles in an agglomeration process, for example in a fluidised-bed reactor. Preferably, the agglomeration is carried out in any of the well-known fluidised bed dryers equipped with a product container. The process is started with the fluidisation of the core particles. The outer matrix emulsion may be formed by mixing with high shear Inclusions $I_2$ comprising fragrance material and optionally carrier $C_1$, with an aqueous phase comprising water, matrix substance $S_2$ and emulsifier $E_2$. The matrix emulsion may thereafter be sprayed onto the fluidised core particles using a pressure, sonic or a pneumatic nozzle, preferably, a two-fluid nozzle, which is inserted either on the top (top spray), lateral (lateral spray), tangential (tangential spray), or at the bottom (bottom spray) of the fluidised bed. The lateral position of the nozzle is preferred in the present invention.

Surprisingly it has been found that increasing the nozzle pressure over a certain value described below, while keeping other process parameters constant, leads to certain advantages. In particular, it has been surprisingly found that high atomisation air pressures not only decreases the size of the feed droplets exiting the nozzle but also narrows the ultimate particle size distribution of the particulate material formed. Furthermore, it has been surprisingly found that with high atomisation air pressures, not only the size distribution of the particulate material can be controlled but also the retention of very volatile components can be generally enhanced, yielding retention values of volatile substances as high as 95% in weight. Thus, under fast agglomeration conditions the atomisation air pressure is preferably from 0.1 to 3.0 bar, more preferably from 0.5 to 2.5 bar, while, if slow agglomeration is required, for example in a batch process, the pressure is preferably set between 2.0 to 8.0 bar, most preferably from 4.0 to 6.0 bar. Therefore, it is possible to obtain a narrow particle size distribution with conventional fluidised bed granulators.

The process of the present invention permits of the preparation of a composition comprising more than 25%, preferably more than 30%, more preferably 40 to 60% of a fragrance material and the loss of said fragrance material during granulation may be less than 15%, preferably less than 10%, and is therefore cost effective.

The core particles used in a process as hereinabove described may be prepared with a very high loading of Inclusions $I_1$, by spray drying, extrusion, and compaction or directly by radical polymerization, polycondensation or polyaddition. However, spray drying is a preferred preparation method.

In a preferred spray-drying method, the core particles are prepared by emulsifying the core particle inclusions $I_1$ with an aqueous phase consisting of water, core particle matrix material $S_1$ and emulsifier $E_1$. The amount of emulsifier is chosen such that the Inclusion $I_1$ is dispersed in the form of small droplets in the aqueous phase and that the interface between said droplets and the aqueous phase contains sufficient emulsifier $E_1$ in order to provide a stable oil-in-water feed emulsion for spray drying purposes. This may be achieved by adopting a mass ratio $I_1$:$E_1$ of less than 25:2 for typically available modified starch emulsifiers. This mass ratio ensures the formation of a stable dispersion of very fine Inclusions $I_1$ that permit of optimal initial fragrance retention during the spray drying process and also reduce the tendency for fragrance material to leach out of the composition and collect at the surface of the composition (that is, the minimisation of surface fragrance or so-called "surface oil").

The spray drying process may be carried out using rotating disk or nozzle atomisers such as air pressure nozzles or two-fluid nozzles or a rotating disk, into a co-current hot air drying chamber. Suitable equipment for the production of the emulsion is a batch, high shear propeller inserted into a stirring vessel of appropriate volume size. Alternatively a high-pressure mixer can be used. The mean droplet size of the Inclusions $I_1$ is preferably below 5 micron, more particularly below 1 micron, in order to achieve the advantages referred to in the preceding paragraph. This small droplet size may be achieved by applying either a combination of starch-based material and sugar with an emulsifier $E_1$ which is starch-based, or high efficiency encapsulation systems using polymers of synthetic origin, e.g. poly(vinyl alcohol), poly (vinyl alcohol-co-acetate) copolymers, or other suitable emulsifiers and carrier materials.

The skilled person will appreciate that the process of forming a composition of the present invention may be performed on an industrial scale using a batch process or alternatively a continuous process.

The core particles so formed may have particle sizes between 0.01 and 1.0 mm, more particularly 0.05 and 1.0 mm, preferably between 0.1 mm and 0.4 mm, most preferably between 0.1 mm and 0.3 mm.

The amount of a composition employed in a consumer product according to the present invention will depend on the nature of that consumer product, e.g. body care products, household products and laundry products, e.g. detergents or fabric softeners and the like, and on the use to which it is intended. In powder detergent systems, the composition may be employed above 0.01%, generally between 0.05 to 2.5% by weight of the powder, more typically 0.2 to 1.0%, depending on the kind of powder detergent system, e.g. either concentrated or standard, and on the nature of the fragrance components.

In particular, powder detergents optionally coloured for visual effect, may be formed comprising fragrance material at 0.35% to 0.5% by weight. Such a composition, compared with compositions wherein fragrance oil is added directly to the powder detergent material, displays substantial benefits in terms of storage stability and reductions in loss of perfume when stored at 37° C. and 70% relative humidity for one month. Compositions of the present invention also display controlled release of fragrance material during the wash cycle and enhanced deposition of fragrance materials onto fabrics. Additionally, in-use tests with consumer panellists confirm the hedonic benefits, in that fabrics treated with a product containing a composition according to the invention were judged more fresh and clean than those compositions wherein fragrance material was added directly. Optionally, the detergent compositions may be formed as tablets and have the same advantages as hereinbefore described.

Further specific applications for compositions according to the inventions are in toilet tablets, bath salts, toilet cleaners, abrasives, candles and cosmetic products. Further, compositions may be added to non-aqueous deodorants and antiperspirant roll-on products. Still further, compositions may be mixed with conventional water-absorbing material in diapers, wherein the release of perfume is induced by high humidity in the water-absorbing material due to body fluids.

In addition to being provided in admixture with consumer products, the composition may be used alone, for example as a laundry freshening product, which may be added to a detergent composition prior to use, or alternatively added to a washing machine prior to commencement of a laundry cycle. Such a composition has an advantage of flexibility in that the user may select a particular hedonic character that it wishes to impart to the detergent composition.

Compositions, whereas being described in the context of fragrance applications may additionally be employed in food applications. Compositions can be used to impart a special effect of highly concentrated flavours or the use of more than one flavour within the same particulate material to give a special sensation feeling clearly distinguishable during consuming like a cooling and sparkling effect together with a rounded fruity impression.

Other applications, in addition to flavour or fragrance applications may be contemplated, for example the compositions may include such materials as olfactory compounds, bio-active materials such as insect, cockroach and acarian repellents, bactericides and bacteriostatic agents, cosmetic agents or any organic volatile or reactive liquid useful in flavour or fragrance applications. By the expression <<olfactory compounds>> is meant a masking agent or a precursor thereof, or flavour and fragrance precursors.

The compositions of the present invention are particularly suitable for delivering volatile and chemically sensitive flavour components. Flavoured particles may provide a higher stability of the flavour during storage in food products and flavour burst upon chewing the food. The present invention is particularly interesting for delivering flavour materials that are reactive with each other as the reactive components may be separated between core particles or between core particles and outer matrix. Flavour components that may be employed alone or in combination in the inclusions $I_1$ include components having a Loss Factor greater than $10^2$ Pa ppm, for example 2-Methyl Pyrazine, Acetophenone Extra, Alcohol C6, Alcohol C8, Aldehyde C7 Heptylic, Aldehyde C8, Aldehyde C9, Allyl Caproate, Amyl Butyrate, Anisicaldhyde, Benzaldehyde, Benzyl Acetate, Benzyl Alcohol, Benzyl Butyrate, Benzyl Formate, Benzyl Iso Valerate, Benzyl Propionate, Butyl Acetate, Camphor, Cinnamic Aldehyde, Cis-3-Hexenol, Cis-3-Hexenyl Acetate, Cis-3-Hexenyl Formate, Cis-3-Hexenyl Propionate, Citronellal, Citronellol, Cuminic Aldehyde, Damascenone, Damascone Alpha, Damascone Beta, Diethyl Malonate, Dimethyl Anthranilate, Dimethyl Benzyl Carbinyl Acetate, Estragole, Ethyl Acetate, Ethyl Aceto Acetate, Ethyl Benzoate, Ethyl Heptoate, Ethyl Salicylate, Ethyl-2-Methyl Butyrate, Eucalyptol, Eugenol, Fenchyl Acetate, Fenchyl Alcohol, Methyl-2-octynoate, 2-sec-Butylcyclohexanone, Styralyl Acetate, Hexyl Acetate, Ionone Alpha, Iso Amyl Acetate, Iso Butyl Acetate, Iso Menthone, Jasmone Cis, Laevo Carvone, Linalool, Linalool Oxide, Melonal, Menthol, Menthone, Methyl Acetophenone, Methyl Amyl Ketone, Methyl Benzoate, Methyl Heptenone, Methyl Hexyl Ketone, Methyl Para Cresol, Methyl Phenyl Acetate, Methyl Salicylate, Neral, Nerol, Para Cresol, Para Cresyl Acetate, Para Tolyl Aldehyde, Phenyl Acetaldehyde, Phenyl Ethyl Acetate, Phenyl Ethyl Butyrate, Phenyl Ethyl Formate, Phenyl Ethyl Iso Butyrate, Phenyl Ethyl Propionate, Phenyl Propyl Acetate, Phenyl Propyl Aldehyde, 4-Methyl-2-(2-methyl-1-propenyl)tetrahydropyran, Styralyl Propionate, Terpineol, Terpinolene, Trans-2-Hexenal, Flavour components that may be employed alone or in combination in inclusions $I_2$ may be those components having a Loss Factor less than $10^2$ Pa ppm, for example Hexyl Cinnamic Aldehyde Alpha, Oxacycloheptadec-10-en-2-one, Linalyl Benzoate, Cedrol, Benzyl Cinnamate, Linalyl Cinnamate, Phenyl Ethyl Cinnamate, Para Cresyl Phenyl Acetate, Benzyl Salicylate, Hexyl Salicylate, Phenyl Ethyl Salicylate, Oxacyclohexadecan-2-one.

Thus, the compositions according to the invention may also be employed in foodstuffs, for example in dry soups and sauces, instant products, bakery products (cakes, bread specialities, bread mixes, pancake mixes, cake mixes), savoury and meat products, pasta, hot and cold beverages (for instance flavoured tea), pharmaceutical applications (powders, capsules and tablets), cereals, chewing gum and confectionery products. Compositions may be employed in these applications to provide to the product treated from 1 to 10% by weight of flavour materials.

Figure 1:
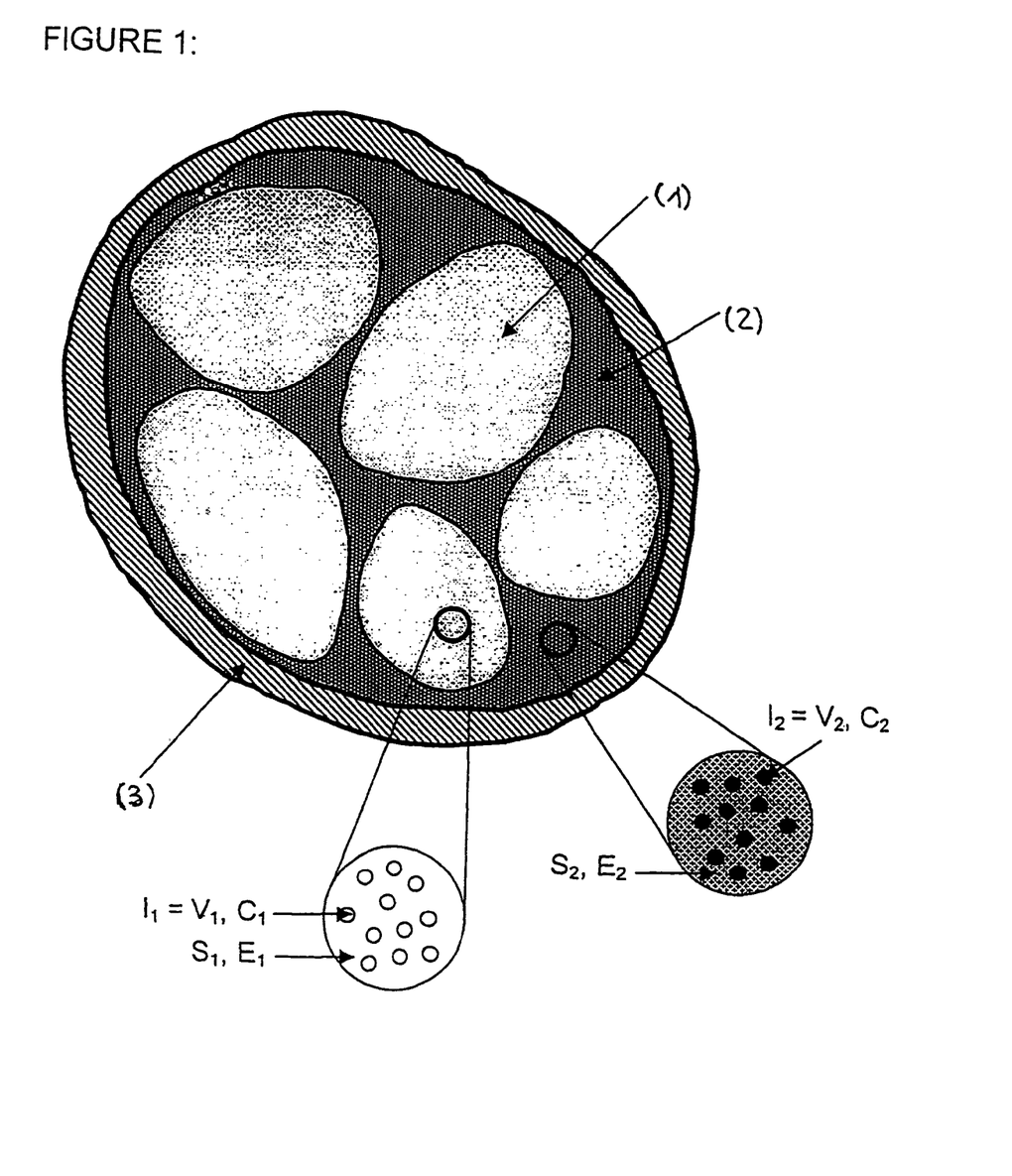
FIG. 1 shows a composition comprising an outer matrix comprising a hydrophilic matrix substance S2 containing inclusions I2, which comprise a fraction of the fragrance material and discrete core particles embedded in the outer matrix comprising a hydrophiic matrix substance S1 containing inclusions I1 which comprise the remaining components of the fragrance material.

In FIG. 1 the structure of a preferred embodiment of the composition according to the present invention is shown. The core particles (1) are embedded in an outer matrix (2). The composition is provided with a coating (3). The core particles (1) are formed of a substance $S_1$ which may be solid, water- or alkali-soluble or swellable, and non-porous, and an emulsifier $E_1$. The core particles (1) additionally comprise inclusions $I_1$. Said inclusions comprise components of a fragrance material and a carrier material $C_1$. The outer matrix (2) comprises a matrix substance $S_2$ and an emulsifier $E_2$. Dispersed within $S_2$ are Inclusions $I_2$. Said inclusions $I_2$ comprise components of fragrance material and a carrier $C_2$.

There now follows a series of Examples that serve to illustrate the invention.

EXAMPLE 1

Preparation of a Composition Having Perfumed Core Particles and Perfumed Outer Matrix.

Perfumed core particles were prepared by spray drying on a standard multistage dryer (APV Nordic Anhydro, Denmark) with a water evaporation capacity of 80 kg/h. A core particle emulsion was produced using 69.3 kg of a maltodextrin having a Dextrose Equivalent (DE) of 6, 18.9 kg of Capsul® (National Starch Ltd., UK), 154 kg water, and 37.8 kg of a standard fragrance oil used in detergent compositions (Givaudan Vernier SA, Switzerland). The emulsion was prepared according to a procedure wherein the aforementioned ingredients were slowly added together under vigorous stirring (15500 rpm) with a polytron turbine (Kinematica AG, Switzerland). Once mixed, the mixture was further homogenised for an additional 10 minutes until a stable emulsion was obtained having a mean particle size below 1 micron. The process parameters where selected such that only little agglomeration occurred by choosing an inlet temperature of 190° C., a fluidised bed air inlet temperature of 85° C. and a fluidised bed product temperature of 65° C. The resulting odorised core particles exhibited a fragrance load (so-called <<total oil>> load) of 30 wt %, as measured by HPLC, resulting in an initial retention of 99%, and a particle size distribution of $D(v,0.1)=81$ μm, $D(v,0.5)=154$ μm, $D(v,0.9)=258$ μm. Particle size is represented here by volume average diameter ($D(v,x)$) wherein <<x>> denotes the volume fraction of particles having an average diameter below $D(v,x)$.

6.54 kg of said odorised core particles were placed in a conical fluidised bed granulator WS-GT-0.40 (Allgaier Werke GmbH, Germany). An outer matrix emulsion was prepared using 2.3 kg of a polyvinyl alcohol, which has a degree of hydrolysation of 88% and a degree of polymerization of 630, 3.1 kg of standard detergent fragrance oil (Givaudan Vernier SA, Switzerland), and 9.3 kg of water, according to a procedure as described in the preceding paragraph. Said outer matrix emulsion was then sprayed onto the core particles in a fluidised bed by applying an atomisation air pressure of 5 bar with a spraying rate of up to 11 kg per hour, using a laterally-inserted two-fluid nozzle (Schlick Modell 0/2, Duesen-Schlick GmbH, Germany). The inlet temperature was 77° C., outlet temperature 55° C. Thereafter, 12.0 kg of the resultant composition in the form of a particulate material were covered with 6.7 kg aqueous solution of 20 wt % of the same polyvinyl alcohol as used for the outer matrix to form a coating over the particulate material. This yielded 13.3 kg of particulate material wherein the dry matter of the coating related to 11% of the theoretical yield of the particulate material. After screening (2.0 mm sieve), the bulk density was found to be 0.34 g cm$^{-3}$, and the particulate material was dust-free and free flowing. The particle size distribution was narrow: D (v,0.1) =711 μm, D (v,0.5)=1281 μm, D (v,0.9)=2019 μm. The particulate material disintegrated within 10 min in a stirred standard wash liquor at 40° C. The total fragrance (so-called <<total oil>>) measured by HPLC was 30 wt % (theoretical perfume load 38 wt %) with an initial retention of 79%.

EXAMPLE 2

Illustrating the Effect of Separating Fragrance Components Between Core Particles and Outer Matrix In this example, fragrance material components are divided between core particles and outer matrix. The selection is made such that fragrance components having a loss factor of $F_L>10^2$ Pa ppm are present in core particles whereas the components having a loss factor of $F_L<10^2$ Pa ppm are present in the outer matrix. Such a composition is then compared with a composition wherein total fragrance material is provided in an outer matrix, the core particles being fragrance material-free.

EXAMPLE 2.1

Whole Fragrance Material in Outer Matrix 14.0 kg of coarse sugar were placed as unperfumed core particles in a conical fluidised bed granulator WS-GT-0.40 (Allgaier Werke GmbH, Germany). The outer matrix emulsion was prepared according to Example 1 using 11.3 kg of water, 7.1 kg of Hi-Cap 100® (National Starch Ltd., UK), 1.8 kg of mannitol and 0.18 kg triacetin, and 11.3 kg of a standard detergent fragrance oil (Givaudan Vernier SA, Switzerland). Granulation of these particles was performed according to the method of Example 1 by atomising the outer matrix emulsion using a lateral inserted two-fluid nozzle (as in Example 1). The nozzle diameter is 2.2 mm; nozzle pressure is 5.0 bar; feed rate is 6–9.5 kg/h; air inlet temperature is 70–78° C.; and air outlet temperature is 56–65° C.

The resultant product was dried for 15 minutes before cooling down to 30° C.

16.0 kg of the product was put in the product container and coated with 1.6 kg of a vegetable fat having a melting point between 42 and 44° C. were heated to 70° C. and sprayed onto the product choosing following process parameters: Nozzle configuration: as above; Fluidisation air: ambient temperature; and Feed rate: 2.5–3 kg/h.

After a protective screening step (2.0-mm sieve) a dust-free and free-flowing product resulted with a bulk density of 0.68 g/cm³. The particle size distribution of said product was narrow: $D(v,0.1)=505$ µm, $D(v,0.5)=756$ µm, $D(v,0.9)=1211$ µm.

Additionally, the particulate material had a total oil load of 23 wt % (by NMR) with an initial retention of 79%. The final particulate material disintegrated within 10 minutes in a stirred standard wash liquor of 40° C.

EXAMPLE 2.2

Fragrance Material Divided between Core Particles and Outer Matrix

A spray-dried perfumed core material was produced on a Niro Mobile Minor (Niro A/S, Denmark). Preparation of core particle feed emulsion was conducted by dissolving 0.714 kg of maltodextrin MD02 having a DE between 11–14, and 0.195 kg of Capsule® (National Starch Ltd., UK), in 1.111 kg water at 60° C. After cooling down to ambient temperature 0.390 kg of the detergent fragrance oil used in above Example 2.1 were emulsified according to a procedure analogous to Example 1. Eleven of such prepared feed emulsions were spray dried using the following process parameters:

Inlet temperature: 180° C.; Outlet temperature: 90° C.; Feed rate: 4.6 kg/h; and Rotary Disk Atomiser speed: 18,000 rpm.

The eleven spray dried batches were mixed together and the resulting perfumed core particles exhibited a total oil load of 26% (w/w) (by NMR) resulting in an initial retention of 87%. Said core particles had a particle size distribution of $D(v,0.1)=11$ µm, $D(v,0.5)=29$ µm, $D(v,0.9)=77$ µm. 8.95 kg of said perfumed core particles were placed in a conical fluidised bed granulator WS-GT-0.40 (Allgaier Werke GmbH). The outer matrix emulsion was prepared according to a procedure analogous to Example 1 by using 3.20 kg of water, 1.98 kg of Hi-Cap 100® (National Starch Ltd., UK), 0.50 kg mannitol and 0.05 kg triacetin, and 1.93 kg of the remaining components of the fragrance material used in Example 2.2 having a loss factor $F_L$ smaller than $10^2$ Pa ppm. The granulation process was performed on said fluidised bed equipment by atomising and spraying 7.7 kg of the outer matrix emulsion onto said core particles using the following process parameters: Air inlet temperature: 79–85° C.; Air outlet temperature: 43–53° C.; Nozzle diameter (lateral inserted): 2.2 mm; Nozzle pressure: 2.0 bar; Feed rate: 2.1–10.7 kg/h; Nozzle type: As Example 1.

The coating procedure was conducted as in Example 1, wherein 12.0 kg of product was coated with 1.2 kg of a vegetable fat having a melting point between 42 and 44° C. pre-heated to 70° C. However, the process parameters were chosen as follows:

Nozzle configuration: same as above; Fluidisation air: ambient temperature; Feed rate: 3.4 kg/h. As in previous Examples, the particulate material was sieved by using a mesh size of 2.0 mm, whereas the coated particles had a perfume content of 28 wt % (by NMR) with an initial retention of 97%. The particle size distribution of said product was found to be as follows: $D(v,0.1)=88$ µm, $D(v,0.5)=218$ µm, $D(v,0.9)=454$ µm, with a bulk density of 0.52 g/cm³. The composition disintegrated within 10 minutes in a stirred standard wash liquor at 40° C.

In the following table, the data demonstrate the effectiveness of dividing the whole fragrance material into two distinct parts between the core particles (CP) and outer matrix (M) according to the selection criteria set forth above. The retention of certain fragrance material components after the granulation process was measured by GC/MS analysis.

| Fragrance components | Divided CP | Divided M | Undivided M | Divided. Initial Retention [%] | Undivided. Initial Retention [%] | Loss Factor $F_L$ [Pa ppm] |
|---|---|---|---|---|---|---|
| Component A | x | | X | 97 | 48 | 22447 |
| Terpineol | x | | X | 95 | 49 | 15255 |
| Tetrahydro linalool | x | | X | 97 | 47 | 3466 |
| Component B | x | | X | 96 | 49 | 1024 |
| Citronellol | x | | X | 100 | 53 | 761 |
| Aldehyde C10 | x | | X | 93 | 44 | 424 |
| Component C | x | | X | 98 | 7 | 290 |
| Beta ionone | | x | X | 100 | 75 | 90 |
| Dihydro beta ionone | | x | X | 84 | 56 | 84 |
| Component D | | x | X | 84 | 65 | 4.55 |
| Cyclohexyl salicylate | | x | X | 94 | 91 | 1.37 |
| Component E | | x | X | 85 | 75 | 0.55 |
| Benzyl benzoate | | x | X | 88 | 99 | 0.30 |
| Component F | | x | X | 89 | 99 | 0.11 |
| Component H | | x | X | 92 | 100 | 0.09 |

The results demonstrate that the initial retention of the components with high Loss Factor (so called <<Top Notes>>) is much higher when the components are divided and included in the core particles, compared with compositions wherein the total fragrance material is incorporated in the outer matrix.

EXAMPLE 3

Effect of Coating on "Aged Retention" of Fragrance Material

Compositions were prepared substantially as set out in Example 1 wherein one composition was provided with a coating and the other not.

Compositions were incorporated into standard, unperfumed detergent bases resulting in 130.00 g perfumed powder detergent with a perfume level of 0.35 wt % based on total powder detergent. As a reference, 0.46 g of free perfume was incorporated into 129.54 g of the same standard detergent base. Both samples and reference were filled separately into carton boxes, sealed and stored in a climate chamber at 70% relative humidity and 37° C. for 1 month. All samples were compared in terms of aged fragrance material profile measured by GC/MS analysis. The results are tabulated below.

| Fragrance Components | Retention free perfume [%] | Retention Without coating [%] | Retention With coating [%] |
|---|---|---|---|
| Limonene | 0 | 18 | 41 |
| Component A | 32 | 42 | 80 |
| Phenyl ethyl alcohol | 25 | 36 | 72 |
| Tetrahydro linalool | 33 | 50 | 84 |
| Benzyl acetate | 0 | 26 | 50 |
| Citronellol | 26 | 18 | 71 |
| Linalyl acetate | 8 | 39 | 80 |
| Component B | 18 | 41 | 79 |
| Component G | 29 | 53 | 92 |
| Gamma methyl ionone | 49 | 51 | 91 |
| Lilial | 4 | 36 | 65 |
| Hexyl salicylate | 18 | 47 | 94 |
| Component H | 56 | 61 | 100 |
| Component I | 0 | 52 | 94 |
| Average | 21 | 41 | 78 |

The results demonstrate that there is a significant improvement of the protection during storage with samples having a coating.

Standard machine wash tests were performed using the following procedure: Terry towels (2.5 kg) were washed in standard wash machines (1 wash cycle, 10 liters water) followed by 2 rinse cycles (27 liters water) at 50° C. using 130 g of sample powder described above. Olfactory evaluation was done on wet towels by a panel of experts. Results for the composition of Example 1 are given below, whereas the scale was as follows: best=7, worst=1.

| Samples | Retention |
|---|---|
| Aged Reference (0.35% free perfume) | 3.5 |
| Aged Sample (0.35% in composition of invention) | 6.5 |
| Fresh Reference (0.35% free perfume) | 7.0 |

The results demonstrate the protective power of the compositions according to the invention during storage under high humidity conditions.

EXAMPLE 4

Deposition of Fragrance Material on Fabrics

The deposition of fragrance material components on dried towels, washed under the same conditions as in EXAMPLE 3, was measured by thermodesorption followed by GC/MS analysis. For this example the composition of Example 1 was compared to free perfume. Values are given in <<relative excess deposition percentage>>, defined as the ratio of the amount of fragrance material component deposited from the detergent containing compositions to that from the detergent containing the free perfume.

| Key Fragrance Components | relative excess deposition [%] |
|---|---|
| Component B | 366 |
| Lilial | 143 |
| Terpineol | 117 |
| Alpha ionone | 97 |
| Component C | 78 |
| Hexyl salicylate | 75 |
| Benzyl acetate | 60 |
| Component H | 52 |
| Diphenyloxide | 48 |
| Aldehyde C12 MNA | 39 |
| Component J | 15 |
| Eucalyptol | 13 |

These results show that more fragrance components are present on the terry towel after drying, which is consistent with a much better deposition from the wash liquor. This excess deposition is attributed to the particular fragrance material component's release profile.

The invention claimed is:

1. A particulate composition for delivering a fragrance material consisting of a an outer matrix comprising a hydrophilic matrix substance S2 containing inclusions I2 which comprise a fraction of the components of the fragrance material, and disposed within the outer matrix, discrete core particles comprising a hydrophilic matrix substance S1 containing inclusions I1 which comprise the remaining components of the fragrance material, and further optionally comprising a coating material.

2. A particulate composition according to claim 1 wherein at least 70% of the components of the fragrance material in the core particles have a loss factor $F_L$ higher than $10^2$ Pa ppm.

3. A particulate composition according to claim 1 wherein at least 70% of components of the fragrance material in the outer matrix material have a loss factor $F_L$ lower than 100 Pa ppm.

4. A particulate composition according to claim 3 wherein core particles comprise a hydrophilic matrix substance $S_1$ and the outer matrix comprises a hydrophilic matrix substance $S_2$ which are independently selected from the group of carbohydrates, natural or synthetic gums, chitin or cationic polysaccharides, cellulose or cellulose derivatives, polypeptides, synthetic water soluble or partially water soluble or degradable polymers, polyelectrolytes, biodegradable biopolymers, plasticizers or inorganic materials.

5. A particulate composition according to claim 3 wherein the composition contains carrier $C_1$ and the carrier $C_2$, wherein $C_1$ and $C_2$ are independently selected from the group consisting of hydrophobic liquid diluents, waxes, resins, surfactants, silicones and modified silicones, polyolefines or other synthetic polymers.

6. A particulate composition according to claim 1 wherein the discrete core particles comprise a hydrophilic matrix substance $S_1$ having disposed therein inclusion $I_1$ and optionally an emulsifier $E_1$ wherein $I_1$ comprises components of a fragrance material and optionally a carrier material $C_1$ for the fragrance material.

7. A particulate composition according to claim 6 comprising up to 80% by weight of inclusions $I_1$ or up to 75% by weight of the matrix inclusions $I_2$.

8. A particulate composition according to claim 6 wherein inclusions $I_1$ comprises 30 to 100% by weight of components of a fragrance material, or inclusions $I_2$ comprises 30 to 100% by weight components of a fragrance material.

9. A particulate composition according to claim 6 wherein the ratio $I_1:E_1$ or the ratio $I_2:E_2$ is lower than 25:2 (w/w).

10. A particulate composition according to claim 9 wherein the emulsifier E1 and/or E2 is a modified starch.

11. A particulate composition according to claim 10 wherein the modified starch is a combination of octenyl succinate-substituted starch and non-substituted starch.

12. A particulate composition according to claim 6 wherein the inclusions have a mean particle size of 0.1 to 20 microns.

13. A particulate composition according to claim 1 wherein the outer matrix comprises a hydrophilic matrix substance $S_2$ having disposed therein inclusion $I_2$ and optionally an emulsifier $E_2$ wherein $I_2$ comprises components of a fragrance material and optionally a carrier material $C_2$ for the fragrance material.

14. A particulate composition according to claim 1 comprising at least 25% by weight of fragrance material.

15. A particulate composition according to claim 1 further comprising a coating, which coats the outer matrix of the whole particle, which comprises a fat, a fatty acid, a hydrophobized silicon dioxide, a silicone, a silicone-based wax or a mixture thereof, a modified cellulose, a poly(vinylalcohol-co-vinyl acetate) copolymer, a partially lactonized poly(vinyl alcohol-co-acrylic acid) copolymer, a modified poly(vinyl alcohol) comprising acetate groups, or a mixture thereof.

16. A particulate composition according to claim 15 wherein the coating has a melting point between 35 and 95° C.

17. A particulate composition according to claim 1 wherein the fragrance material comprises components having a loss factor of greater than 5 Pa ppm.

18. The composition according to claim 1 wherein the material has a particle size of 0.1 to 2 mm.

19. A consumer product comprising a particulate composition according to claim 1 wherein the consumer product is selected from the group consisting of laundry products, body care products, household products, food and beverage products.

20. A laundry freshener product comprising a particulate composition as defined in claim 1.

21. A process for preparing a particulate composition according to claim 1 comprising the step of spraying the outer matrix material onto core particles formed of particle matrix to encapsulate said particles.

22. A process according to claim 21 wherein the core particles are prepared by forming an oil-in-water emulsion of fragrance material, matrix material $S_1$, water optional emulsifier $E_1$ and optional carrier material $C_1$, and spray-drying the emulsion to form the core particles.

* * * * *